United States Patent [19]

Chandraratna

[11] Patent Number: 5,278,318

[45] Date of Patent: Jan. 11, 1994

[54] PROCESS OF SYNTHESIZING ACETYLENES DISUBSTITUTED WITH A PHENYL GROUP AND A 2-SUBSTITUTED CHROMANYL, THIOCHROMANYL OR 1,2,3,4-TETRAHYDROQUINOLINYL GROUP

[75] Inventor: Roshantha A. S. Chandraratna, El Toro, Calif.

[73] Assignee: Allergan, Inc., Irvine, Calif.

[21] Appl. No.: 964,227

[22] Filed: Oct. 21, 1992

Related U.S. Application Data

[60] Division of Ser. No. 749,747, Aug. 26, 1991, Pat. No. 5,162,546, which is a division of Ser. No. 594,882, Oct. 9, 1990, abandoned, which is a continuation-in-part of Ser. No. 409,488, Sep. 19, 1989, Pat. No. 4,980,369.

[51] Int. Cl.$^5$ ............... C07D 311/04; C07D 335/06
[52] U.S. Cl. ......................... 549/23; 549/347; 549/374; 549/407; 549/453
[58] Field of Search ................ 549/23, 347, 374, 407, 549/453

[56] References Cited

U.S. PATENT DOCUMENTS

| | | | |
|---|---|---|---|
| 4,096,341 | 6/1978 | Frazer | 560/85 |
| 4,695,649 | 9/1987 | Magami et al. | 562/480 |
| 4,739,098 | 4/1988 | Chandraratna | 560/8 |
| 4,740,519 | 4/1988 | Shroot et al. | 549/57 |
| 4,810,804 | 3/1989 | Chandraratna | 549/23 |
| 4,826,969 | 5/1989 | Maignam et al. | 560/100 |
| 4,855,320 | 8/1989 | Chatterjee et al. | 549/313 |
| 4,895,868 | 1/1990 | Chandraratna | 549/23 |
| 4,980,369 | 12/1990 | Chandraratna | 549/23 |
| 4,992,468 | 2/1991 | Chandraratna | 560/9 |
| 5,006,550 | 4/1991 | Chandraratna | 514/456 |
| 5,013,744 | 5/1991 | Chandraratna | 546/290 |
| 5,015,658 | 5/1991 | Chandraratna | 549/23 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 546/269 |
| 5,053,523 | 10/1991 | Chandraratna | 549/398 |
| 5,162,546 | 11/1992 | Chandraratna | 549/23 |
| 5,175,185 | 12/1992 | Chandraratna | 514/445 |

FOREIGN PATENT DOCUMENTS

| | | |
|---|---|---|
| 130795 | 1/1985 | European Pat. Off. . |
| 176034 | 4/1986 | European Pat. Off. . |
| 3708060 | 9/1987 | Fed. Rep. of Germany . |

OTHER PUBLICATIONS

E. Negishi et al., *Journal of Organic Chemistry*, 45(12), pp. 2526-2528 (1980).

(List continued on next page.)

*Primary Examiner*—Richard L. Raymond
*Attorney, Agent, or Firm*—Gabor L. Szekeres; Martin A. Voet; Robert J. Baran

[57] ABSTRACT

Retinold-like activity is exhibited by compounds of the formula

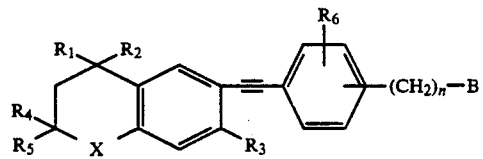

where X is S, O; $R_1$, $R_2$ and $R_3$ are hydrogen or lower alkyl; $R_4$ and $R_5$ are hydrogen or lower alkyl with the proviso that $R_4$ and $R_5$ cannot both be hydrogen, $R_6$ is hydrogen, lower alkyl, lower alkenyl, lower cycloalkyl or halogen; n is 0–5, and B is H, —COOH or a pharmaceutically acceptable salt, ester or amide thereof, —CH$_2$OH or an ether or ester derivative, or —CHO or an acetal derivative, or —COR$_1$ or a ketal derivative where R$_1$ is —(CH$_2$)$_m$CH$_3$ where m is 0–4, or a pharmaceutically acceptable salt thereof.

3 Claims, No Drawings

OTHER PUBLICATIONS

S. Takahashi et al., *Synthesis* pp. 627–630 (1980).

H. Kagechika et al., *Journal of Medicinal Chemistry*, 31(11), pp. 2182–2192 (1988).

A. King et al., *Journal of Organic Chemistry*, 43(2), pp. 358–360 (1978).

K. Shudo et al., *Chem. Pharm. Bull.*, 33(1), pp. 404–407 (1985).

M. Sporn et al. *Journal of the American Academy of Dermatology*, 15, pp. 756–764 (1986).

"The Merck Index" 11th ed., S. Budavari, ed., entry 2257, p. 350 Merck & Co., Inc. (1989).

C. Naylor, Jr. et al., *J. Am. Chem. Soc.*, 53, pp. 4114–4119 (1953).

G. Frey et al., *Chemical Abstracts* 105:153320r p. 717, abstract of DE 3,433,946 (1986).

S. Davies et al., *Journal of Organometallic Chemistry*, 387, pp. 381–390 (1990).

A Dopamine Receptor Model and Its Application in the Design of a New Class of Rigid Pyrrolo[2,3-g]isoquinoline Antipsychotics, Gary L. Olson, et al. *American Chemical Society*, 1981, vol. 24, No. 9, pp. 1026–1031.

6.2.3 Conformational Restriction, Williams, et al., *Drug Discovery and Development*, 1987 The Humana Press, pp. 54–55.

V. Retinoid Structure–Biological Activity Relationships, Chemistry and Biology of Synthetic Retinoids, pp. 324–356.

PROCESS OF SYNTHESIZING ACETYLENES DISUBSTITUTED WITH A PHENYL GROUP AND A 2-SUBSTITUTED CHROMANYL, THIOCHROMANYL OR 1,2,3,4-TETRAHYDROQUINOLINYL GROUP

CROSS-REFERENCE TO RELATED APPLICATION

1. This application is a divisional of application Ser. No. 07/749,747 filed on Aug. 26, 1991 issued as U.S. Pat. No. 5,162,546, which is a divisional of application Ser. No. 07/594,882, filed on Oct. 9, 1990, now abandoned, which is itself a continuation-in-part of application Ser. No. 409,488, filed on Sep. 19, 1989, which is now U.S. Pat. No. 4,980,369 and is assigned to the same assignee as this application.

BACKGROUND

Field of the Invention

2. This invention relates to novel compounds having retinoid-like activity. More specifically, the invention relates to compounds having an ethynylbenzoic acid portion and a second portion which is a 2-substituted tetrahydroquinolinyl, thiochromanyl, or chromanyl group. The acid function may also be converted to an alcohol, aldehyde or ketone or derivatives thereof, or may be reduced to —$CH_3$.

Related Art

Carboxylic acid derivatives useful for inhibiting the degeneration of cartilage of the general formula 4-(2-(4,4-dimethyl-6-X)-2-methylvinyl)benzoic acid where X is tetrahydroquinolinyl, chromanyl or thiochromanyl are disclosed in European Patent Application 0133795 published Jan. 9, 1985. See also European Patent Application 176034A published Apr. 2, 1986 where tetrahydronaphthalene compounds having an ethynylbenzoic acid group are disclosed, and U.S. Pat. No. 4,739,098 where three olefinic units from the acid-containing moiety of retinoic acid are replaced by an ethynylphenyl functionality.

SUMMARY OF THE INVENTION

This invention covers compounds of Formula 1

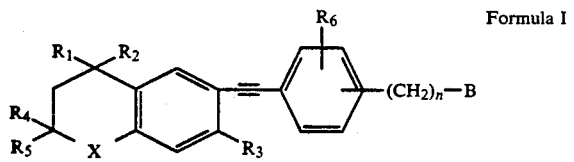

Formula I wherein X is S, O; $R_1$–$R_3$ are hydrogen or lower alkyl, $R_4$ and $R_5$ are hydrogen or lower alkyl with the proviso that $R_4$ and $R_5$ cannot both be hydrogen; $R_6$ is lower alkyl, lower alkenyl, lower cycloalkyl having 1 to 6 carbons, or halogen; n is 0–5; and B is H, —COOH or a pharmaceutically acceptable salt, ester or amide thereof, —$CH_2OH$ or an ether or ester derivative, or —CHO or an acetal derivative, or —$COR_1$ or a ketal derivative where $R_1$ is an alkyl, cycloalkyl or alkenyl group containing 1 to 5 carbons.

In a second aspect, this invention relates to the use of the compounds of Formula I for treating dermatoses, such as acne, Darier's disease, psoriasis, icthyosis, eczema, atopic dermatitis and epithelial cancers. These compounds are also useful in the treatment of arthritic diseases and other immunological disorders (e.g. lupus erythematosus), in promoting wound healing, in treating dry eye syndrome and in reversing the effects of sun damage to skin.

This invention also relates to a pharmaceutical formulation comprising a compound of Formula 1 in admixture with a pharmaceutically acceptable excipient.

In another aspect, this invention relates to the process for making a compound of Formula 1 which process comprises reacting a compound of Formula 2 with a compound of Formula 3 in the presence of cuprous iodide and $Pd(PQ_3)_2Cl_2$ (Q is phenyl) or a similar complex

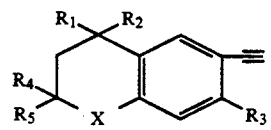

Formula 2

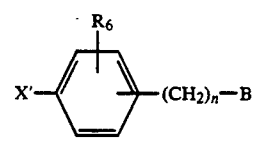

Formula 3 where $R_1$–$R_6$ are the same as described above, X' is a halogen, preferably I; and n is the same as defined above; and B is H, or a protected acid, alcohol, aldehyde or ketone, giving the corresponding compound of Formula 1; or to the process of making a compound of Formula 1 which consists of reacting a zinc salt of Formula 4 with a compound of Formula 3 in the presence of $Pd(PQ_3)_4$ (Q is phenyl) or a similar complex.

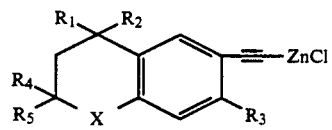

Formula 4 where $R_1$–$R_6$, and X, are the same as defined above, giving the corresponding compound of Formula 1; or homologating a compound of the Formula 5

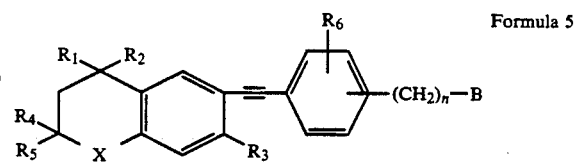

Formula 5 where n is 0–4 to give an acid of Formula 1; or
converting an acid of Formula 1 to a salt; or
forming an acid addition salt;
converting an acid of Formula 1 to an ester; or
converting an acid of Formula 1 to an amide; or
reducing an acid of Formula 1 to an alcohol or aldehyde;
or
converting an alcohol of Formula 1 to an ether or ester;
or
oxidizing an alcohol of Formula 1 to an aldehyde; or
converting an aldehyde of Formula 1 to an acetal; or
converting a ketone of Formula 1 to a ketal.

GENERAL EMBODIMENTS

Definitions

The term "ester" as used here refers to and covers any compound falling within the definition of that term as classically used in organic chemistry. Where B (of Formula 1) is —COOH, this term covers the products derived from treatment of this function with alcohols, preferably with aliphatic alcohols having 1-6 carbons. Where the ester is derived from compounds where B is —CH$_2$OH, this term covers compounds of the formula —CH$_2$OOCR where R is any substituted or unsubstituted aliphatic, aromatic or aliphatic-aromatic group, preferably with 1-6 carbons in the aliphatic portions.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids or alcohols. Here, and where ever else used, lower alkyl means having 1-6 carbon atoms and includes straight as well as branched chain alkyl groups. Also preferred are the phenyl or lower alkylphenyl esters.

Amide has the meaning classically accorded that term in organic chemistry. In this instance it includes the unsubstituted amides and all aliphatic and aromatic mono-and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formula —CK where K is (—OR)$_2$. Here, R is lower alkyl. Also, K may be —OR$_1$O— where R$_1$ is lower alkyl of 2-5 carbon atoms, straight chain or branched.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of this invention are those where the ethynyl group and the B group are attached to the 1 and 4 positions respectively of a benzene ring (i.e. where the phenyl moiety of the compound is para substituted) n is 0; and B is —COOH, an alkali metal salt or organic amine salt, or a lower alkyl ester thereof, or —CH$_2$OH and the lower alkyl esters and ethers thereof, or —CHO and acetal derivatives thereof. The more preferred compounds shown in Formula 6 are:

ethyl 4-[(2,2,4,4-tetramethylthiochroman-6-yl)-ethynyl] benzoate (Compound 1 X=S, R$_3$=H, R$_4$=CH$_3$, R$_5$=CH$_3$, R''=C$_2$H$_5$);

4-[(2,2,4,4-tetramethylthiochroman-6-yl)-ethynyl] benzoic acid (Compound 2, X=S, R$_3$=H, R$_4$=CH$_3$, R$_5$=CH$_3$, R''=H);

ethyl 4-[(2,2,4,4-tetramethylchroman-6-yl)-ethynyl] benzoate (Compound 3, X=O, R$_3$=H, R$_4$=CH$_3$, R$_5$=CH$_3$, R''=C$_2$H$_5$);

4-[(2,2,4,4-tetramethylchroman-6-yl)-ethynyl] benzoic acid (Compound 4, X=O, R$_3$=H, R$_4$=CH$_3$, R$_5$=CH$_3$, R''=H);

ethyl 4-[(2,2,4,4,7-pentamethylthiochroman-6-yl)-ethynyl] benzoate (Compound 5, X=S, R$_3$=CH$_3$, R$_4$=CH$_3$, R$_5$=CH$_3$, R''=C$_2$H$_5$);

4-[(2,2,4,4,7-pentamethylthiochroman-6-yl)-ethynyl] benzoic acid (Compound 6, X=S, R$_3$=CH$_3$, R$_4$=CH$_3$, R$_5$=CH$_3$, R''=H)

ethyl 4-[(2,2,4,4,7-pentamethylchroman-6-yl)-ethynyl] benzoate (Compound 7, X=O, R$_3$=CH$_3$, R$_4$=CH$_3$, R$_5$=CH$_3$, R''=C$_2$H$_5$);

4-[(2,2,4,4,7-pentamethylchroman-6-yl)-ethynyl] benzoic acid (Compound 8, X=O, R$_3$=CH$_3$, R$_4$=CH$_3$, R$_5$=CH$_3$, R''=H)

ethyl-4[(2,4,4,trimethyl-6-thiochromanyl)ethynyl]benzoate (Compound 56, X=S, R$_3$=H, R$_4$H, R$_5$=CH$_3$, R''=C$_2$H$_5$)

4-(2,4,4,trimethyl-6-thio-chromanyl)-ethynyl benzoic acid (Compound 57, X=S, R$_3$=H, R$_4$=H, R$_5$=CH$_3$, R''=H)

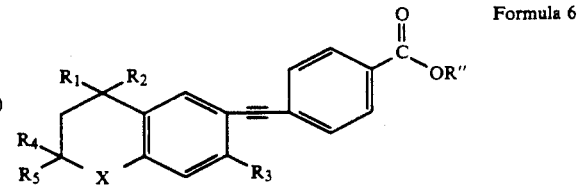

Formula 6

The compounds of this invention may be administered systemically or topically, depending on such considerations as the condition to be treated, need for site-specific treatment, quantity of drug to be administered, and similar considerations.

In the treatment of dermatoses, it will generally be preferred to administer the drug topically, though in certain cases such as treatment of severe cystic acne, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation containing between 0.001 and 5 percent by weight, preferably about 0.01 to 1% will usually constitute a therapeutically effective concentration. If administered systemically, an amount between 0.01 and 100 mg per kg body weight per day, but preferably about 0.1 to 10 mg/kg, will effect a therapeutic result in most instances.

The retionic acid like activity of these compounds was confirmed through the classic measure of retionic acid activity involving the effects of retionic acid on ornithine decarboxylase. The original work on the correlation between retinoic acid and decrease in cell proliferation was done by Verma & Boutwell, *Cancer Research*, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-O-tetradecanoylphorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in *Cancer Res.*, 35: 1662–1670, 1975.

By way of example of retinoic acid-like activity it is noted that in the assay conducted essentially in accordance with the method of Verma & Boutwell, ibid, the following examples of the preferred compounds of the present invention (Compounds 1, 3 and 7) attained an 80% inhibition of TPA induced ODC activity at the following concentrations ($IC_{80}$):

| Compound | $IC_{80}$ conc (nmols) |
|---|---|
| 1 | 1.2 |
| 3 | 0.1 |
| 7 | 1.0 |
| 56 | 2.2 |
| 57 | .24 |

SPECIFIC EMBODIMENTS

The compounds of this invention can be made by a number of different synthetic chemical pathways. To illustrate this invention, there is here outlined a series of steps which have been proven to provide the compounds of Formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

Compounds of Formula 1 where X is —S— and $R_4$ and $R_5$ are hydrogen or lower alkyl, with the proviso that $R_4$ and $R_5$ both are not hydrogen, are prepared as per Reaction Scheme I

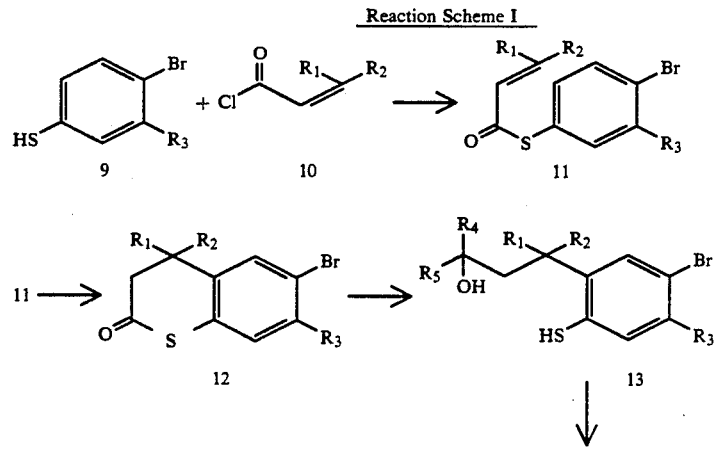

-continued

Reaction Scheme 1

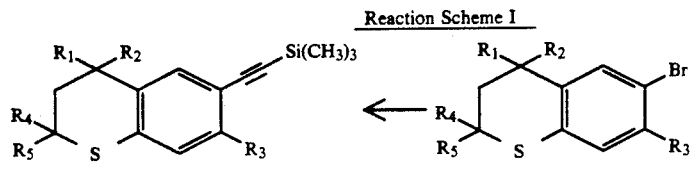

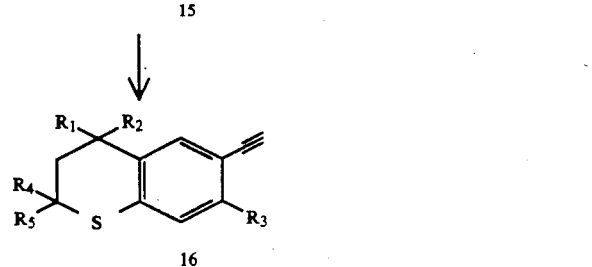

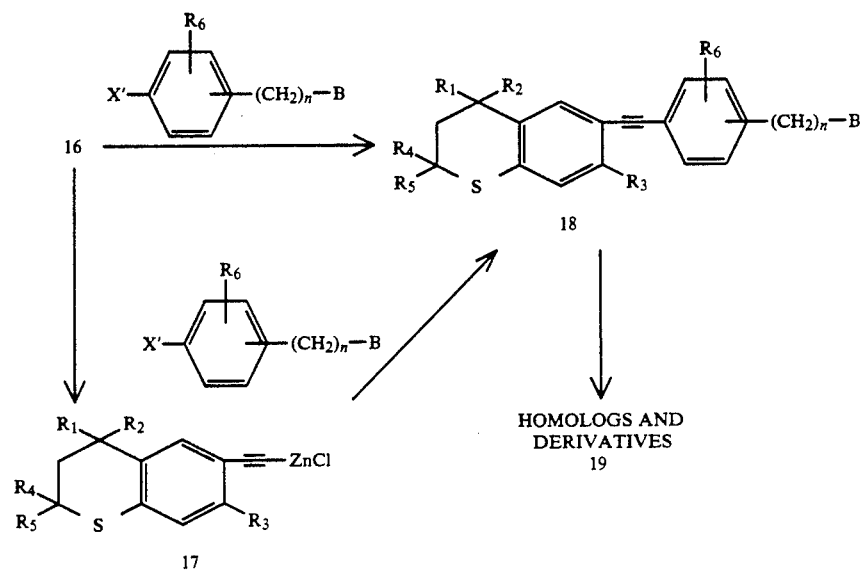

In Reaction Scheme I, $R_1$-$R_3$ are hydrogen or a lower alkyl group, $R_6$ is defined as above in connection with Formula 1, n is 0-5 and B is H, or a protected acid, alcohol, aldehyde or ketone. X' is Cl, Br or I when n is 0 but preferably be Br or I when n is 1-5.

Compounds of Formula 1 where X is oxygen and $R_4$ and $R_5$ are hydrogen or lower alkyl, with the proviso that $R_4$ and $R_5$ both are not hydrogen, are prepared as per reaction Scheme 2.

Reaction Scheme 2

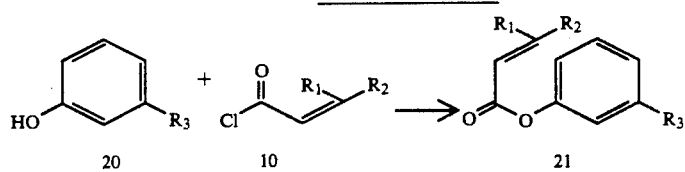

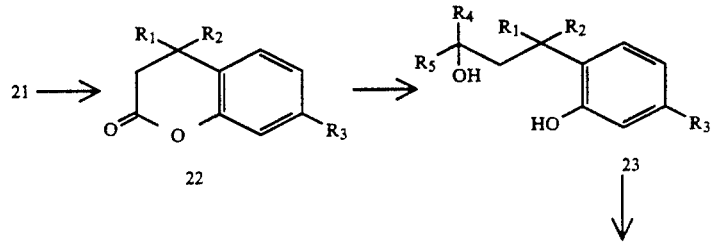

Reaction Scheme 2

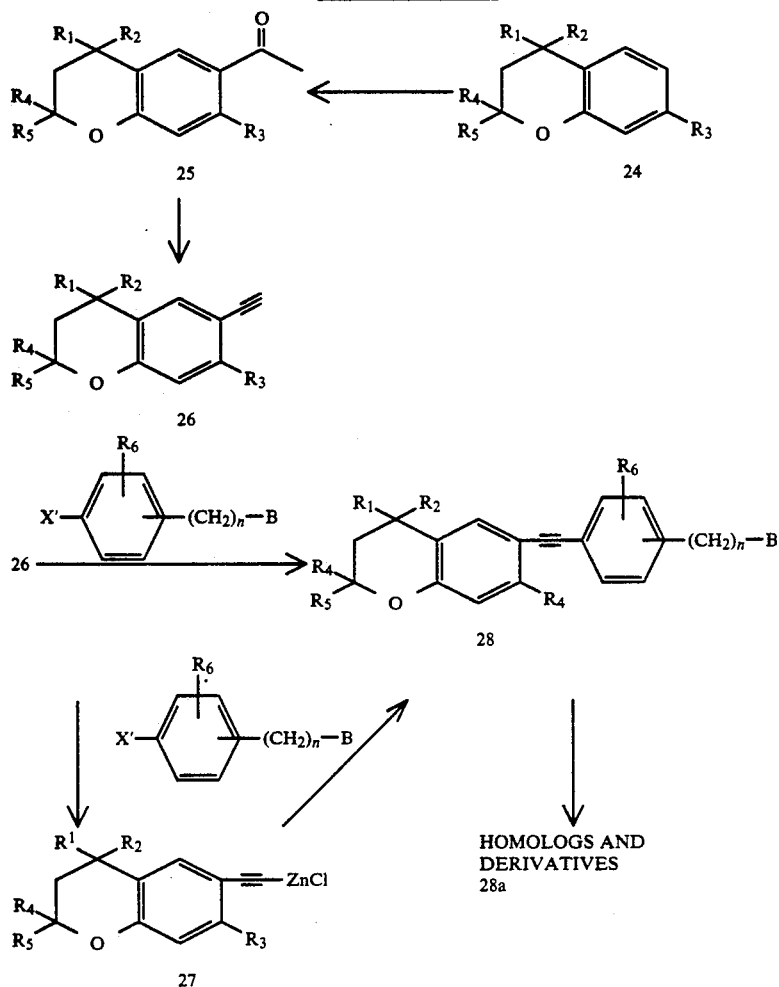

In Reaction Scheme 2 the definitions of $R_1$–$R_6$, n, B and X' are the same as in Reaction Scheme 1.

A general description of the synthetic steps outlined in Reaction Schemes 1 and 2 is as follows.

In Reaction Scheme 1 the 4-bromo-thiophenol (Compound 9) is acylated with an acylating agent, such as an acid chloride (Compound 10) derived from an appropriately substituted acrylic acid. The acylation is conducted in an inert solvent (such as tetrahydrofuran) in the presence of strong base (for example sodium hydride). The resulting thioester (Compound 11) which contains the olefinic bond of the acrylic acid moiety is ring closed in the presence of a Friedel Crafts type catalyst (such as aluminum chloride) by stirring in a suitable solvent such as methylene chloride. The resulting 2-oxo-6-bromothiochroman (Compound 12) is usually isolated in crystalline form.

The $R_4$ and/or $R_5$ substituents (both of which cannot be hydrogen in accordance with the invention) are introduced by treating the 2-oxo-6-bromo-thiochroman (Compound 12) with a Grignard reagent, bearing the alkyl substituents $R_4$ and $R_5$ (such as methylmagnesium bromide when $R_4$ and $R_5$ are methyl). When the Grignard reagent (such as methylmagnesium bromide) is in excess, the thiochroman ring is opened and the tertiary alcohol derivative of the 4-bromo thiophenol (Compound 13) is formed.

Ring closure of the thiophenol derivative (Compound 13) which has the desired $R_1$, $R_2$, $R_3$, $R_4$ and $R_5$ substituents, is affected by heating in acidic conditions, preferably by heating Compound 13 in aqueous acid. The resulting 6-bromothiochroman which bears the desired alkyl (or hydrogen) substituents, $R_1$, $R_2$, $R_3$, $R_4$ and $R_5$ is shown as compound 14 in Reaction Scheme 1.

To introduce the acetylene (ethyne) portion into the molecule, the substituted 6-bromothiochroman 14 is reacted with trimethylsilylacetylene in the presence of cuprous iodide and a suitable catalyst, typically having the formula $Pd(PQ_3)_2Cl_2$ (Q is phenyl). The reaction is typically conducted in the presence of bis(triphenylphosphine) palladium (II) chloride catalyst, an acid acceptor, (such as triethylamine) under an inert gas (argon) atmosphere, by heating in a sealed tube. The resulting 6-trimethylsilylethynylthiochroman is shown as Compound 15 in Reaction Scheme 1.

As is shown on Reaction Scheme 1, the trimethylsilyl moiety is removed from the 6-trimethylsilylethynyl-thiochroman 15 in the next synthetic step, to provide the ring substituted 6-ethynyl-thiochroman derivative (Compound 16). The latter reaction is conducted under basic conditions, preferably under an inert gas atmosphere.

In order to introduce the phenyl or substituted phenyl substituent on the acetylene (ethyne) portion of Compound 16, Compound 16 is coupled with the reagent X'—Q—(CH$_2$)$_n$—B (Formula 3, Q is a di- or multisubstituted phenyl residue) where the symbols n, X' and B have the same meaning as defined in connection with Formula 3. In other words, the phenyl or substituted phenyl substituent is introduced into the 6-ethynyl-thiochroman 16 by reacting the latter with a halogen substituted phenyl compound (Formula 3) in which the benzene nucleus either has the desired substituent [(CH$_2$)$_n$—B] or wherein the actual substituent (CH$_2$)$_n$—B can be readily converted to the desired substituent by means of organic reactions well known in the art.

Coupling of the 6-ethynyl-thiochroman 16 with the reagent X'—Q—(CH$_2$)$_n$—B is affected directly in the presence of cuprous iodide, a suitable catalyst, typically of the formula Pd(PQ$_3$)$_2$Cl$_2$ and an acid acceptor, such as triethylamine, by heating in a sealed tube under an inert gas (argon) atmosphere.

The resulting disubstituted acetylene compound (Compound 18) may be the target compound made in accordance with the invention, or maybe readily converted into the target compound by such steps as salt formation, esterification, deesterification, homologation, amide formation and the like. These steps are further discussed below.

Compound 18 may also be obtained by first converting the 6-ethynyl-thiochroman derivative 16 into the corresponding metal salt, such as a zinc salt, (Compound 17) and thereafter coupling the salt 17 with the reagent X'—Q—(CH$_2$)$_n$—B (Formula 3 Q is phenyl or substituted phenyl residue) in the presence of a catalyst having the formula Pd(PQ$_3$)$_4$ (Q is phenyl), or similar complex.

Derivatization of Compound 18 is indicated in Reaction Scheme 1 as conversion to "homologs and derivatives", Compounds 19.

More specifically with respect to either derivatization or deblocking of protected functionalities in Compound 18, or with respect to the preparation of phenyl derivatives of the formula X'—Q—(CH$_2$)$_n$—B, (which after coupling either directly yield the compounds of the invention, or are readily converted into them) the following is noted.

Where a protected phenyl derivatives is needed to couple with the compounds of Formula 2 (Compounds 16 in Reaction Scheme 1), such may be prepared from their corresponding acids, alcohols, ketones or aldehydes. These starting materials, the protected acids, alcohols, aldehydes or ketones, are all available from chemical manufacturers or can be prepared by published methods. Carboxylic acids are typically esterified by refluxing the acid in a solution of the appropriate alcohol in an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of n before effecting a coupling reaction, where such compounds are not available from a commercial source, the phenyl derivatives where B is —COOH are subjected to homologation by successive treatment under Arndt-Eistert conditions or other homologation procedures. Alternatively, phenyl derivatives where B is different from COOH, may also be homologated by appropriate procedures. The homologated acids can then be esterified by the general procedure outlined in the preceding paragraph.

An alternative means for making compounds where n is 1–5 is to subject the compounds of Formula 1, where B is an acid or other function, to homologation, using the Arndt-Eistert method referred to above, or other homologation procedures.

The acids and salts derived from Formula 1 are readily obtainable from the corresponding esters. Basic saponification with an alkali metal base will provide the acid. For example, an ester of Formula I may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about $-10$ degrees and $+10$ degrees C. The last mentioned solution is then stirred at the reduced temperature for 1–4 hours, preferably 2 hours. Solvent removal provides a residue which is taken up in an inert inorganic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexlcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds where B is H can be prepared from the corresponding halogenated benzene compounds, preferably where the halogen is I.

With reference to Reaction scheme 2, phenol, or a phenol substituted in the 3 (meta) position by an alkyl substituent ($R_3$) (Compound 20) is acylated with an acylating agent, such as an acid chloride (Compound 10) derived from an appropriately substituted acrylic acid. In Reaction Scheme 2, just as in Reaction Scheme 1, the $R_1$ and $R_2$ substituents of the target compounds are introduced through this acrylic acid derivative 10. The acylation with the acid chloride 10 is preferably conducted in the presence of a strong base (e.g. sodium hydride) in an inert solvent (such as tetrahydrofuran). The resulting substituted phenyl-acrylate is shown in Reaction Scheme 2 as Compound 21.

The substituted phenyl-acrylate 21 is ring closed under Friedel Crafts type reaction conditions ($AlCl_3$ catalyst, in an inert solvent, such as methylene chloride) to provide the 2-oxo-chroman compound (Compound 22) which bears, in the 4-position, the $R_1$ and $R_2$ substituents and in the 6-position the $R_3$ substituent (as applicable). Just like the analogous 2-oxo-thiochroman 12 in Reaction Scheme 1, the 2-oxo-chroman 22 of Reaction Scheme 2 is treated with a Grignard reagent to introduce the $R_4$ and $R_5$ substituents. As it was noted out above, $R_4$ and $R_5$ both cannot be hydrogen. When $R_4$ and $R_5$ are methyl, the Grignard reagent is preferably methylmagnesium chloride (dissolved in tetrahydrofuran, THF). A solution of Compound 22 in a suitable solvent, for example in dry diethylether is added to this Grignard reagent. The resulting phenol containing a tertiary alcohol side chain, (that is a molecule in which the chroman ring had been opened) is shown in Reaction Scheme 2 as Compound 23.

Compound 23 which already has the desired $R_1$, $R_2$, $R_3$, $R_4$ and $R_5$ substituents, is ring closed under acidic conditions, (e.g. by heating in aqueous sulfuric acid) to provide the chroman derivative (Compound 24). It should be noted that up to this point in the synthetic sequence (which is preferably but not necessarily exclusively used for making the compounds of the invention) similar or analogous steps are involved for making both the thiochroman (Reaction Scheme 1) and chroman derivatives (Reaction Scheme 2), the only difference being that in Reaction Scheme 2 the starting phenol derivative does not have a halogen (such as a bromo) substituent.

Because of the lack of the halogen substituent in the preferred synthetic sequence for preparing the chroman compounds of the invention, the preferred and herein illustrated steps (Reaction Scheme 2) for introducing the acetylene (ethyne) group into the 6-position of the chroman moiety are different from the steps utilized for introducing the acetylene moiety into the analogous thiochroman (Reaction Scheme 1).

Thus, in Reaction Scheme 2 an acetyl group is introduced into the 6-position of the chroman derivative 24 under Friedel-Crafts type conditions. This acetylation is preferably conducted with acetyl chloride, in nitromethane solvent, in the presence of aluminum chloride.

The resulting 6-acetylchroman derivative is Compound 25.

The acetylenic (triple) bond is introduced into the molecule by converting the 6-acetyl moiety of chroman 25 to an acetylene moiety. This is accomplished, preferably, by treatment with lithium diisopropylamide (at low temperature, such as $-78$ degrees C.) which causes enolization of the acetyl group. The intermediate enol compound (not shown in Reaction scheme 2) is esterified by treatment with diethylchlorophosphate (or the like) and is again reacted at reduced temperature (e.g. $-78$ degrees C.) with lithium diisopropylamide, to form the triple bond (presumably by an elimination reaction) and to yield the 6-ethynyl-chroman derivative (Compound 26).

It is noted at this point that the present invention is not intended to be limited or bound by the above-mentioned and other theories of reaction mechanisms. Brief description of theory of reaction mechanisms (where applicable) are given to further enable and facilitate the work of a skilled artisan in the field to modify and adjust the synthetic conditions to fit particular specific intermediates and to make the several compounds of the invention, without departing from the scope and spirit of the invention.

Referring back again to Reaction scheme 2, the 6-ethynylchroman derivative 26 may be converted into the target compounds of the invention in synthetic steps which are analogous to the conversion of 6-ethynyl-thiochromans (Compound 16) into the corresponding target thiochroman derivatives (see Reaction Scheme 1). Briefly, Compound 26 is preferably heated with a reagent $X'$—Q—$(CH_2)_n$—B (Formula 3 Q is phenyl or substituted phenyl residue) in the presence of cuprous iodide, a suitable catalyst, typically of the formula $Pd(PQ_3)_2 Cl_2$ (Q is phenyl or the like) and an acid acceptor, such as triethylamine. This coupling reaction, yields the target chroman compounds, (Compound 28) or such derivatives which are readily converted into the target compounds by protection, deprotection, esterification, homologation etc., as is discussed in connection with Reaction Scheme 1. The homologs are indicated, as a group, as Compound 28a in Reaction Scheme 2.

Alternatively, the 6-ethynyl-chroman compounds 26 may first be converted to the corresponding metal (zinc) salt (Compound 27) and thereafter coupled with the reagent $X'$—Q—$(CH_2)_n$—B (Formula 3 Q is phenyl substituted phenyl residue) under conditions which are similar to the conditions described in Reaction scheme 1 for coupling of Compounds 18 with the same reagent.

REACTION SCHEME 3

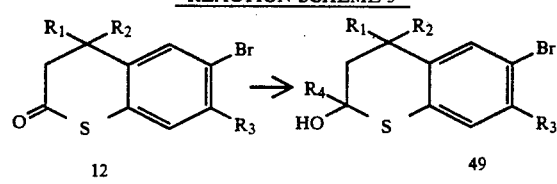

-continued
REACTION SCHEME 3

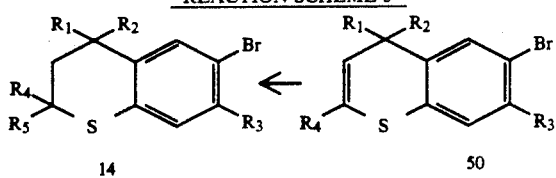

REACTION SCHEME 4

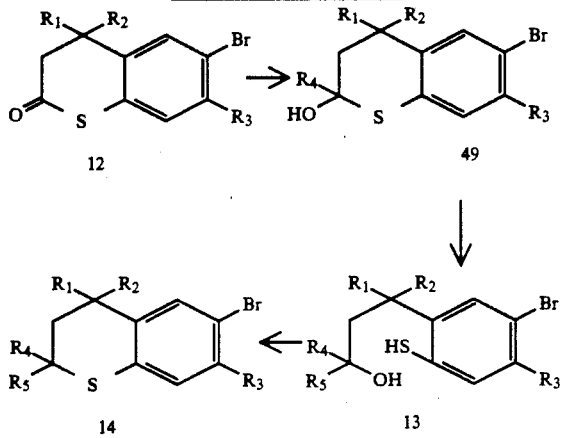

REACTION SCHEME 5

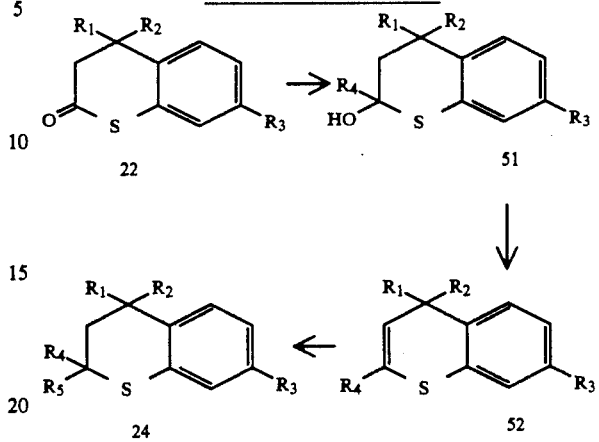

REACTION SCHEME 4

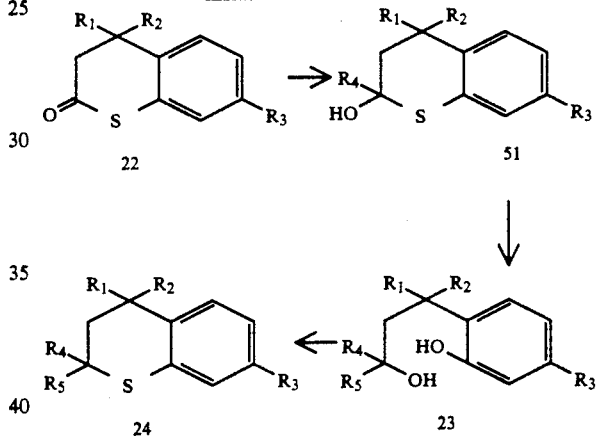

Referring to Reaction Scheme 3 substituted 6-bromothiochroman 14, where the $R_4$ or $R_5$ substituent is alkyl and the other is hydrogen can be made by treating the 2-oxo-6-bromo-thiochroman (Compound 12) with a Grignard reagent. As in Reaction Scheme 1 the 2-oxothiochroman 12 is subjected to an excess of Grignard reagent, bearing the alkyl substituents $R_4$ or $R_5$ (such as methylmagnesium bromide when $R_4$ or $R_5$ is methyl). However, the reaction temperature is controlled to and maintained at a relatively low temperature (such as $-14$ degrees C.) and the duration of the reaction is kept relatively short (0.5 hours). A hemiacetal derivative of 4-bromothiophenol (Compound 49) is formed in this controlled Grignard reaction, as shown in Reaction Scheme 3. Cyclization of the thiophenol derivative Compound 49 is affected by heating in acidic conditions, preferably by aqueous acid, to give the unsaturated thio olefin (Compound 50). The 6-bromothioolefin (Compound 50) is reduced by hydrogenation in the presence of palladium sulfide-on-carbon catalyst at increased pressure (approximately 30 psi). The resulting 6-bromo-thiochroman which bears the desired hydrogen and alkyl substituents $R_1$, $R_2$, $R_3$, $R_4$ and $R_5$ with one of $R_4$ or $R_5$ being hydrogen, is shown as Compound 14.

Again, referring to 6-bromo-thio chroman, 14, in Reaction Scheme 4 the $R_4$ and $R_5$ substituents, both of which are alkyl but not identical with one another in this example, are introduced by treating the hemiacetal derivative (Compound 49) with a different Grignard reagent than previously used, as shown in Scheme 4. In this Grignard reaction the thio chroman ring is opened and the tertiary alcohol derivative of 4-bromothiophenol, 13, is formed. Ring closure of the thiophenol derivative 13 which has the desired $R_1$, $R_2$, $R_3$, $R_4$ and $R_5$ substituents, is affected by heating in acidic conditions, preferably by heating with aqueous acid. The resulting 6-bromo thiochroman which bears the desired alkyl and hydrogen substituents $R_1$, $R_2$, $R_3$, $R_4$ and $R_5$ is shown as Compound 14.

In Reaction Scheme 5, just as in Reaction Scheme 3, one of the $R_4$ or $R_5$ substituents is alkyl and the other is hydrogen. Just like the analogous 2-oxo-thiochroman 12 in Reaction Scheme 3, the 2-oxochroman 22 of Reaction Scheme 5 is treated with Grignard reagent to introduce the $R_4$ and $R_5$ substituents. With controlled reaction temperature and time, the resulting hemiacetal derivative can be isolated as Compound 51, as shown in Reaction Scheme 5. Under acidic conditions (e.g. by heating in aqueous acid) the hemiacetal 51 is cyclized to form the corresponding olefin derivative (Compound 52). The olefin derivative can then be reduced using the same conditions as described in connection with Reaction Scheme 3 for the reduction of Compound 49, or by a more general reducing procedure. The resulting chroman derivative is shown as Compound 24 in Reaction Scheme 5. It should be noted that up to this point in the synthetic sequence (which is preferably but not necessarily exclusively used for making the compounds of the invention) similar or analogous steps are involved for making both the thio-chroman (Reaction Scheme 3) and the chroman derivatives (Reaction Scheme 5) the only difference being that in Reaction Scheme 5 the starting lactone does not have a halogen (such as a bromo substituent).

Referring to Reaction Scheme 6. in Compound 24 of that scheme the $R_4$ and $R_5$ substituents are alkyl but are not identical. The $R_4$ and $R_5$ alkyl substituents are introduced by treating Compound 51 with a different Grignard reagent than previously used to form the tertiary alcohol (Compound 23). The tertiary alcohol 23 which already has the desired $R_1$, $R_2$, $R_3$, $R_4$ and $R_5$ substituents, is ring closed under acidic conditions, as described above, to provide the chroman derivative (Compound 24).

In order to obtain the final acetylenic products where the $R_4$ or $R_5$ substituent is alkyl and the other is hydrogen, or where the $R_4$ and $R_5$ substituents are alkyl but not identical to one another, Compounds 14 and 24 are subjected to substantially the same reaction procedures as outlined in Reaction Scheme 1 and Reaction scheme 2.

The following examples of specific compounds of the invention, and specific examples of the synthetic steps in which the compounds and certain intermediates are made, are set out to illustrate the invention, not to limit its scope.

SPECIFIC EXAMPLES

Ethyl-4-iodobenzoate (Compound 29)

To a suspension of 10 g (40.32 mmol) of 4-iodobenzoic acid in 100 ml absolute ethanol was added 2 ml thionyl chloride and the mixture was then heated at reflux for 3 hours. Solvent was removed in vacuo and the residue was dissolved in 100 ml ether. The ether solution was washed with saturated $NaHCO_3$ and saturated NaCl solutions and dried ($MgSO_4$). Solvent was then removed in vacuo and the residue kugelrohr distilled (100 degrees C.; 0.55 mm) to give the title compound as a colorless oil, PMR ($CDCl_3$): & 1.42 (3 H, t, J~7 Hz), 4,4 (2 H, q, J~7 Hz), 7.8 (4 H).

In the same manner, but substituting for 4-iodobenzoic acid the appropriate acid, the following examples of compounds can be prepared:
ethyl 4-iodophenylacetate;
ethyl 3-(4-iodophenyl)propionate;
ethyl 4-(4-iodophenyl)butanoate; and
ethyl 5-(4-iodohenyl)pentanoate.

S-(4-bromophenyl) 3.3-dimethylthioacrylate (Compound 30)

To an ice bath cooled solution of 1.92 g (80 mmol) of NaH (obtained from a 60% suspension in mineral oil by 3×15 ml hexane wash) in 30 ml of dry THF was added slowly under argon a solution of 15.1 g (80 mmol) of 4-bromothiophenol in 60 ml of dry THF over 1 h. The mixture was stirred at 0 degrees C. for a further 30 min and then treated with a solution of 10.1 g (85 mmol) of dimethylacryloyl chloride in 30 ml of dry THF. The cooling bath was then removed and the mixture then stirred at room temperature for 40 h. The reaction mixture was poured into 200 ml of water containing 2 ml of glacial acetic acid and the organic layer was separated. The organic layer was washed with 2×75 ml of water and then dried ($MgSO_4$). The solvent was removed in vacuo to give the title compound as a yellow oil. PMR ($CDCl_3$): & 1.91 (3 H, s), 2.14 (3 H, s), 6.03–6.06 (1 H, m), 7.28 (2 H, d, J~8.6 Hz), 7.53 (2 H, d, J~8.6 Hz).

4,4-Dimethyl-6-bromo-2-oxo-thiochroman (Compound 31)

To a stirred, ice-cooled suspension of 15.9 g (119 mmol) of aluminum chloride in 140 ml of methylene chloride was added under nitrogen a solution of 21.64 g (79.9 mmol) of S-(4-bromophenyl) 3,3-dimethyl-thioacrylate (Compound 30) in 100 ml of methylene chloride. The mixture was then stirred at room temperature for 72 h and then poured into 250 g of an ice and brine mixture. The mixture was extracted with methylene chloride and the combined organic extracts were washed with saturated NaCl solution and then dried ($MgSO_4$). The solvent was removed in vacuo and the residue recrystallized from hexanes to give the title compound as white crystals. PMR ($CDCl_3$): & 1.40 (6 H, s), 2.67 (2 H, s), 7.31–7.40 (3 H, m). MS exact mass, m/e 269.9714 (calcd. for $C_{11}H_{11}SOBr$, 269.9714).

4-Bromo-2-(1,1,3-trimethyl-3-hydroxybutyl) thiophenol (Compound 32)

To 3.49 g (32.8 mmol) of lithium perchlorate was added under argon 35 ml of 30M (105 mmol) methyl magnesium bromide in ether. The above mixture was treated dropwise with stirring with a solution of 2.961 g (10.926 mmol) of 4,4-dimethyl-6-bromo-2-oxo-thiochroman (Compound 31) and the reaction mixture was then heated at reflux for 70 h. The reaction mixture was then allowed to cool and poured onto a mixture of 100 g of ice and 8 ml of conc. $H_2SO_4$. The organic layer was separated and the aqueous layer was extracted with 2×25 ml of ether. The organic layers were combined and washed successively with 2×25 ml of saturated $NaHCO_3$ solution, 25 ml of water and 25 ml of saturated NaCl solution and then dried ($MgSO_4$). The solvent was removed in-vacuo and the residue purified by flash chromatography to give the title compound as a pale yellow oil. PMR ($CDCl_3$); & 1.05 (6 H, s) 1.52 (6 H, s), 2.30 (2 H, s), 3.71 (1 H, s), 7.22 (1 H, dd, J~8.5 Hz, 2.1 Hz), 7.28 (1 H, d, J~8.5 Hz), 7.35 (1 H, d, J~2.1 Hz)

Using ethyl magnesium bromide, instead of methyl magnesium bromide, provides the corresponding 4-bromo-2- (1,1 dimethyl 3-ethyl-3-hydroxypentyl)-thiophenol.

2,2,4,4-Tetramethyl-6-bromothiochroman (Compound 33)

A mixture of 500 mg (1.49 mmol) of 4-bromo-2-(1,1,3-trimethyl-3-hydroxybutyl) thiophenol (Compound 32) and 8 ml of 20 percent aqueous $H_2SO_4$ was heated at reflux for 24 h. The mixture was extracted with hexanes, the organic extracts were combined and washed successively with water, saturated $NaHCO_3$, water again, saturated NaCl and then dried ($MgSO_4$). The solvent was removed in vacuo and the residue purified by flash chromatography (silica; hexanes) to give the title compound as a colorless oil. PMR ($CDCl_3$): & 1.35 (6 H, s), 1.40 (6 H, s), 1.93 (2 H, s), 7.17 (1 H, dd, J~8.4 Hz, 2.1 Hz), 7.23 (1 H, d, J~8.4 Hz), 7.26 (1 H, d, J~2.1 Hz). MS exact mass, m/e 284.0221 (calcd. for $C_{13}H_{17}S$ Br, 284.0234).

2,2,4,4-Tetramethyl-6-trimethylsilylethynyl-thiochroman (Compound 34)

A solution of 600 mg (2.11 mmol) of 2,2,4,4-tetramethyl-6-bromothiochroman (Compound 33) in 1.5 ml of triethylamine was placed in a heavy-walled tube and degassed and then treated under argon with 1.4 g (14.3 mmol) of trimethylsilylacetylene and a powdered mixture of 75 mg (0.39 mmol) of cuprous iodide and 150 mg (0.21 mmol) of bis(triphenylphosphine) palladium (II) chloride. The reaction mixture was degassed again, then placed under argon and the tube was sealed. The mixture was heated at 100 degrees C. for 24 h, allowed to cool to room temperature and then treated with a further 1.4 g (14.3 mmol) of trimethylsilylacetylene and a powdered mixture of 75 mg (0.39 mmol) of cuprous iodide and 150 mg (0.21 mmol) of bis(triphenylphosphine) palladium (II) chloride. The mixture was then degassed, placed under argon and then heated in the sealed tube at 100 degrees C. for 96 h. The mixture was cooled to room temperature and extracted with $3 \times 10$ ml of ether. The organic extracts were combined, washed successively with 25 ml of water and 25 ml of saturated sodium chloride solution and then dried ($MgSO_4$). The solvent was removed in vacuo and the residue purified by flash chromatography (silica; hexanes followed by 3% ethyl acetate in hexanes) to give the title compound as a yellow, crystalline solid. PMR ($CDCl_3$): & 0.23 (9 H, s), 1.36 (6 H, s), 1.39,(6 H, s), 1.94 (2 H, s), 7.17 (1 H, dd, J~8.2 Hz, 1.8 Hz), 7.25 (1 H, d, J~1.8 Hz), 7.30 (1 H, d, J~8.2 Hz). MS exact mass, m/1 302.1519 (calcd. for $C_{18}H_{26}$ S Si, 382.1524).

2,2,4,4-Tetramethyl-6-ethynylthiochroman (Compound 35)

To a solution of 527.6 mg (1.75 mmol) of 2,2,4,4-tetramethyl-6-trimethylsilylethynylthiochroman (Compound 34) in 4 ml of isopropanol was added, under argon, 4 ml of 1N KOH solution. The reaction mixture was stirred at room temperature for 20 h and the isopropanol was then removed under vacuum. The residue was extracted with ether and the combined ether extracts were washed successively with water and saturated NaCl solution and then dried ($MgSO_4$). The solvent was removed in vacuo to give the title compound as a yellow oil. PMR ($CDCl_3$): & 1.34 (6 H, s), 1.37 (6 H, s), 1.91 (2 H, s), 2.99 (1 H, s), 7.17 (1 H, dd, J~8.1 Hz, 1.8 Hz), 7.26 (1 H, d, J~1.8 Hz), 7.30 (1 H, d, J~8.1 Hz). MS exact mass, m/e 230.1122 (calcd. for $C_{15}H_{18}S$, 230.1129)

Ethyl 4-[(2,2,4,4-tetramethyl-thiochroman-6-yl)-ethynyl]benzoate (Compound 1)

A solution of 110.7 mg (o.481 mmol) of 2,2,4,4-tetramethyl-6-ethynylthiochroman (Compound 35) and 142.3 mg (0.516 mmol) of ethyl 4-iodobenzoate (Compound 29) in 2 ml of triethylamine was placed in a heavy walled glass tube and degassed under argon. The mixture was then treated with a finely ground mixture of 42 mg (0.221 mmol) of cuprous iodide and 63 mg (0.09 mmol) of bis (triphenylphosphine) palladium (II) chloride. The reaction mixture was degassed under argon again and the tube was sealed. The mixture was stirred at room temperatures for 40 hours. The triethylamine was removed under vacuum and the residue purified by flash chromatography (silica, 3% ethyl acetate in hexanes) to give the title compound as a pale yellow solid. PMR ($CDCl_3$) : & 1.37–1.42 (15 H, m), 1.96 (2 H, s), 4.38 (2 H, q, J~7.0 Hz), 7.25 (1 H, dd, J~8.2 Hz, 1.8 Hz), 7.33 (1 H, d, J~1.8 Hz), 7.37 (1 H, d, J~8.2 Hz), 7.65 (2 H, d, J~8.6 Hz), 8.01 (2 H, d, J~8.6 Hz). MS exact mass, m/e 378.1636 (calcd. for $C_{24}H_{26}O_2S$, 378.165.3).

Using the method for the preparation of Compound 1, but substituting the appropriate ethynylthiochroman (Compound 16 in Reaction Scheme 1) and the appropriate halo substituted phenyl ester (Formula 3, prepared for example as specifically described for Compound 29) the following compounds of the invention may be prepared:

ethyl 4-[(2,2,4,4,7-pentamethylthiochroman-6-yl)-ethynyl]benzoate;
ethyl 4-[(2,2,4,4-tetramethyl-7-ethylthiochroman-6-yl)ethynyl]benzoate;
ethyl 4-[(2,2,4,4-tetramethyl-7-propylthiochroman-6-yl)ethynyl]benzoate;
ethyl 4-[(2,2,4,4-tetramethyl-7-hexylthiochroman-6-yl)ethynyl]benzoate;
ethyl 2-[4-[(2,2,4,4-tetramethylthiochroman-6-yl)ethynyl)-phenyl] acetate;
ethyl 2-[[4-(2,2,4,4,7-pentamethylthiochroman-6-yl)ethynyl)-phenyl]acetate;
ethyl 2-[4(2,2,4,4-tetramethyl-7-ethylthiochroman-6-yl)ethynyl)phenyl]acetate;
ethyl 2-[4(2,2,4,4-tetramethyl-7-hexylthiochroman-6-yl)ethynyl)phenyl]acetate;
ethyl 3-[4-(2,2,4,4-tetramethylthiochroman-2-yl)ethynyl)phenyl]propionate;
ethyl 3-[4-(2,2,4,4,7-pentamethylthiochroman-6-yl)ethynyl)phenyl]propionate;
ethyl 3-[4-2(2,2,4,4-tetramethyl-7-ethylthiochroman-6-yl)ethynyl)phenyl]propionate;
ethyl 3-[4-(2,2,4,4-tetramethyl-7-hexylthiochroman-6-yl)ethynyl)phenyl]propionate;
ethyl 5-[4-(2,2,4,4-tetramethylthiochroman-6-yl)ethynyl)phenyl]pentanoate;
ethyl 5-[4-(2,2,4,4,7-pentamethylthiochroman-6-yl)ethynyl)phenyl]pentanoate;
ethyl 5-[4-(2,2,4,4-tetramethyl-7-ethylthiochroman-6-yl)ethynyl)phenyl]pentanoate;

The positional isomers of the above-noted examples (and of analogous compounds) can also be prepared in accordance with the foregoing procedures or by apparent modifications of such procedures.

Phenyl 3,3-dimethylacrylate (Compound 37)

To an ice bath cooled solution of 1.29 g (54 mmol) of NaH (obtained from a 60% suspension in mineral oil by $3 \times 10$ ml hexane wash) in 20 ml of dry THF was added slowly under oxygen a solution of 5 g (53 mmol) of phenol in 50 ml of dry THF. The mixture was then treated with a solution of 7 g (59 mmol) of dimethylacryloyl chloride in 30 ml of dry THF. The cooling bath was then removed and the mixture was stirred for a further 2.5 h. The reaction mixture was then poured into 150 ml of water containing 1 ml of glacial acetic acid. The mixture was extracted with 150 ml ether and the ether extract washed with saturated NaCl solution and then dried ($MgSO_4$). The solvent was removed in vacuo and the residue purified by flash chromatography (silica; 5% ether in hexanes) to give the title compound as a yellow oil. PMR ($CDCl_3$)): & 1.99 (3 H, s), 2.24 (3 H, s), 5.93 (1 H, broad s), 7.10 (2 H, d, J~7.8 Hz) 7.22 (1 H, t, J~7.8 Hz), 7.38 (2 H, t, J~7.8 Hz).

4,4-Dimethyl-2-oxo-chroman (Compound 38)

To a stirred, ice-cooled suspension of 10.4 g (78 mmol) of aluminum chloride in 160 ml of methylene chloride was added slowly under argon a solution of 7 g (39.8 mmol) of phenyl 3,3-dimethylacrylate (Compound 37) in 40 ml of methylene chloride. The cooling bath was removed and the mixture stirred for a further 42 h. The mixture was poured into a mixture of ice and brine and the organic layer separated. The aqueous layer was extracted with methylene chloride and the organic extracts were combined and washed with saturated NaCl solution and then dried (MgSO₄). The solvent was removed in vacuo and the residue purified by flash chromatography (silica; 10% ether in hexane) to give the title compound as a colorless oil. PMR (CDCl₃: & 1.30 (6 H, s), 2.56 (2 H, s), 7.06 (1 H, dd, J~8.0 Hz, 1.4 Hz), 7.16 (1 H, td, J~8.0 Hz, 1.4 Hz), 7.26 (1 H, td, J~8.0 Hz, 1.7 Hz), 7.33 (1 H, dd, J~8.0 Hz, 1.7 Hz). MS exact mass, m/e 176.0852 (calcd. for C₁₁H₁₂O₂, 176.0837.

2-(1,1,3-Trimethyl-3-hydroxybutyl)phenol (Compound 39)

To 11 ml of 3.0M (33 mmol) methyl magnesium chloride in THF, cooled in an ice bath, was added, under nitrogen, a solution of 1.96 9 (11.1 mmol) of 4,4-dimethyl-2-oxo-chroman (Compound 38) in 35 ml of dry ether. The cooling bath was then removed and the mixture stirred at room temperature for 72 h. The reaction mixture was then poured onto a mixture of 100 g of ice and 3 ml of conc. H₂SO₄ and stirred until the magnesium salts were dissolved. The organic layer was separated and the aqueous layer extracted with 2×50 ml of ether. The organic layers were combined and washed successively with water, saturated NaHCO₃ and saturated NaCl solutions and then dried (MgSO₄). The solvent was removed in vacuo and the residue was purified by flash chromatography (silica; 20% ethyl acetate in hexanes) to give the title compound as a pale yellow solid. PMR (CDCl₃): & 1.13 (6 H, s), 1.48 (6 H, s), 1.89 (1 H, s), 2.23 (2 H, s), 6.60 (1 H, dd, J~7.9 Hz, 1.4 Hz), 6.83 (1 H, s), 6.84 (1 H, td, J~7.9 Hz, 1.4 Hz), 7.07 (1 H, td, J~7.9 Hz, 1.6 Hz), 7.31 (1 H, dd, J~7.9 Hz, 1.6 Hz). MS exact mass, m/e 208.1458 (calcd. for C₁₃H₂₀O₂, 208.1464).

2,2,4,4-Tetramethyl-chroman (Compound 40)

A mixture of 2.98 g (14.3 mmol) of 2-(1,1,3-trimethyl-3-hydroxybutyl) phenol (Compound 39) and 40 ml of 20% aqueous H₂SO₄ was heated at reflux, under nitrogen, for 4 h. The mixture was stirred at room temperature for a further 72 h and then diluted with 50 ml of water. The mixture was extracted with 3×20 ml of hexanes. The organic extracts were then combined and washed successively with water and saturated NaCl solution and then dried (MgSO₄). The solvent was then removed in vacuo to give the title compound as a colorless oil. PMR (CDCl₃): & 1.36 (6 H, s), 1.37 (6 H, s), 1.83 (2 H, s), 6.71 (1 H, dd, J~8.2 Hz, 1.5 Hz) 6.92 (1 H, td, J~8.2 Hz, 1.5 Hz), 7.09 (1 H, td, J~8.2 Hz, 1.5 Hz), 7.29 (1 H, dd, J~8.2 Hz, 1.5 Hz).

2,2,4,4-Tetramethyl-6-acetyl-chroman (Compound 41)

To an ice bath cooled solution of 2 g (10.53 mmol) of 2,2,4,4-tetramethylchroman (Compound 40) in 25 ml of nitromethane was added, under nitrogen, 941 mg (11.99 mmol) of acetyl chloride followed by 1.59 g (11.92 mmol) of aluminum chloride. The cooling bath was then removed and the mixture stirred at room temperature for 16 h. The mixture was then cooled again in an ice bath and treated with 25 ml of conc. HCl. The mixture was then filtered and the residue washed with methylene chloride. The filtrate was concentrated in vacuo and the resultant residue was purified by flash chromatography (silica; 10% ethyl acetate in hexanes) to give the title compound as a yellow oil. PMR (CDCl₃): & 1.38 (6 H, s), 1.39 (6 H, s), 1.87 (2 H, s), 2.56 (3 H, s), 6.83 (1 H, d, J~8.7 Hz), 7.71 (1 H, dd, J~8.7 Hz, 2.1 Hz), 7.98 (1 H, d, J~2.1 Hz). MS exact mass, m/e 232.1468 (calcd. for C₁₃H₂₀O₂, 232.1464).

2,2,4,4-Tetramethyl-6-ethynyl-chroman (Compound 42)

To a cooled (−78 degrees C.) solution of 522 mg (5.17 mmol) of diisopropylamine in 8 ml of dry THF was added slowly, under nitrogen, 3.23 ml of 1.6M (5.17 mmol) n-butyl lithium in hexane. The mixture was stirred at −78 degrees C. for 40 minutes and then treated with a solution of 1.24 g (5.17 mmol) of 2,2,4,4-tetramethyl-6-acetylchroman (Compound 41) in 2 ml of dry THF. The mixture was stirred at −78 degrees C. for a further 1 h and then treated with 895 mg (5.19 mmol) of diethylchlorophosphate. The reaction mixture was allowed to warm to room temperature and transferred by double-ended needle into a solution of lithium diisopropylamide in THF at −78 degrees C. [prepared as described above from 1.04 g (10.34 mmol of diisopropylamine and 6.46 ml of 1.6M (10.34 mmol) of n-butyl lithium in hexane]. The cooling bath was removed and the mixture was stirred at room temperature for 16 h. The mixture was then treated with 10 ml of ice water and acidified to a pH of 2 with 10% HCl. The organic layer was separated and the aqueous layer was extracted with 3×30 ml of pentane. The organic extracts were combined and washed successively with 2×30 ml of dilute HCl, water, 3×30 ml of saturated NaHCO₃ solution and saturated NaCl solution and then dried (MgSO₄). The solvent was removed in vacuo and the residue was purified by flash chromatography (silica; 2% ethyl acetate in hexane) to give the title compound as a pale yellow oil. PMR (CDCl₃): & 1.31 (6 H, s), 1.32 (6 H, s), 1.50 (2 H, s), 3.00 (1 H, s), 6.72 (1 H, d, J~8.4 Hz), 7.20 (1 H, dd, J~8.4 Hz, 2.1 Hz), 7.42 (1 H, d, J~2.1 Hz). MS exact mass, m/e 2.14.1251 (calcd. for C₁₅H₁₈O, 214.1357)

Ethyl 4-[(2,2,4,4-tetramethylchroman-6-yl-ethynyl]benzoate Compound 3)

A solution of 233 mg (1.088 mmol) of 2,2,4,4-tetramethyl-6-ethynyl-chroman (Compound 42) and 308 mg (1.087 mmol) of ethyl 4-iodo-benzoate (Compound 29) in 1 ml of triethylamine was placed in a heavy-walled tube and degassed under argon. The mixture was treated with a finely ground mixture of 50 mg (0.263 mmol) of cuprous iodide and 100 mg (0.142 mmol) of bis (triphenylphosphine) palladium (II) chloride and the tube was then sealed. The reaction mixture was then heated at 55 degrees C. for 48 hours. The triethylamine was removed in vacuo and the residue was purified by flash chromatography (silica, 5% ethyl acetate in hexans) to give the title compound as yellow oil. PMR (CDCl₃) : & 1.33 (6 H, s), 1.34 (6 H, s), 1.37 (3 H, t, J~7.2 Hz), 1.83 (2 H, s), 4.35 (2 H, q, J~7.2 Hz), 6.75 (1 H, d, J~8.4 Hz), 7.24 (1 H, dd, J~8.4 Hz, 2.1 Hz), 7.46 (1 H, d, J~2.1 Hz), 7.54 (2 H, d, J~8.1 Hz), 7.99 (2 H, d, J~8.1 Hz) MS exact mass, m/e 362.1880 (calcd. for C₂₄H₂₆O₃, 362.1881).

3-Methyl-phenyl-3,3-dimethylacrylate (Compound 44)

A 60% suspension of sodium hydride (3.22 g; 81 mmol) in mineral oil was washed with 3×10 ml of hexane and then treated with 30 ml of dry THF. This mixture was cooled in an ice-bath and then treated with a solution of 8.6 g (79.5 mmol) of m-cresol in 80 ml of dry THF. The reaction mixture was stirred for 10 min and then treated with a solution of 10.5 g (88.5 mmol) of dimethylacryloyl chloride in 40 ml of dry THF. The reaction mixture was stirred at room temperature for 96 h and then poured into a mixture of 150 ml of water and 1 ml of glacial acetic acid. The mixture was stirred for 10 min and the organic layer was separated. The aqueous layer was extracted with 2×50 ml of ether. The organic layers were combined and washed successively with water and saturated NaCl solution and then dried (M$_g$SO$_4$). The solvent was removed in vacuo and the residue was purified by flash chromatography (silica; 10% ethyl acetate in hexane) to give the title compound as a pale yellow oil. PMR (CDCl$_3$): & 1.95 (3 H, d, J~1.3 Hz), 2.21 (3 H, d, J~1.2 Hz), 2.34 (3 H, s), 5.90 (1 H, broad S), 6.86–6.93 (2 H, m), 7.01 (1 H, d, J~7.2 Hz), 7.24 (1 H, t, J~7.2 Hz).

2-(1,1,3-Trimethyl-3-hydroxybutyl) 5-methyl-phenol (Compound 45)

To an ice-bath cooled suspension of 13 g (97.5 mmol) of aluminum chloride in 200 ml of methylene chloride was added dropwise under argon a solution of 9.0 g (47.4 mmol) of 3-methyl-phenyl-3,3-dimethylacrylate (Compound 44) in 100 ml of methylene chloride. The reaction mixture was stirred at 0 degrees C. for a further 30 min and then at room temperature for 15 h. The reaction mixture was poured into 200 ml of an ice water/salt mixture and the organic layer was separated. The aqueous layer was extracted with 50 ml of ether. The organic layers were combined and washed successively with water and saturated NaCl solution and then dried (MgSO$_4$). The solvent was removed in vacuo and the residue purified by flash chromatography (silica; 5% ethyl acetate in hexane) to give an approximately 2.5:1 mixture of isomeric products, 4,4,7-trimethyl-2-oxo-chroman and 4,4,5-trimethyl-2-oxo-chroman as a pale yellow oil. To a solution of 3.8 g (20 mmol) of this mixture of isomeric 2-oxo-chromans in 60 ml of ether at 0 degrees C. was added under argon 20 ml of 3.0M (60 mmol) of methyl magnesium bromide in ether. The reaction mixture was stirred at room temperature for 48 h and then poured onto a mixture of ice and 1 ml of conc. H$_2$SO$_4$. The organic layer was separated and the aqueous layer extracted with 2×50 ml of ether. The organic layers were combined and washed successively with water, saturated NaHCO3 solution, water again and then saturated NcCl solution and then dried (MgSO$_4$). The solvent was removed in vacuo and the residue was purified by flash chromatography (silica; 15% ethyl acetate in hexanes) to give the title compound as a colorless oil. PMR (CDCl$_3$): & 1.14 (6 H, s), 1.45 (6 H, s), 2.19 (3 H, s), 2.21 (2 H, s), 6.39 (1 H, d, J~1.8 Hz), 6.67 (1 H, dd, J~7.9 Hz, 1.8 Hz), 7.16 (1 H, d, J~7.9 Hz), 7.44 (1 H, s).

2,2,4,4,7-Pentamethyl-chroman (Compound 46)

To 2.16 g (11.7 mmol) of 2-(1,1,3-trimethyl-3-hydroxybutyl) 5-methyl-phenol (Compound 45) was added under nitrogen 50 ml of 20% aqueous sulfuric acid. The reaction mixture was heated at reflux for 13 h and then cooled. The organic layer was separated and the aqueous layer was extracted with ether. The organic extracts were combined and washed successively with water, saturated NaHCO3 solution, water again and saturated NaCl solution and then dried (MgSO$_4$). The solvent was removed in vacuo to give the title compound as a yellow oil. PMR (CDCl$_3$): & 1.32 (6 H, s), 1.34 (6 H, s), 1.81 (2 H, s), 2.26 (3 H, s), 6.63 (1 H, s), 6.72 (1 H, d, J~7.9 Hz), 7.15 (1 H, d, J~7.9 Hz).

2,2,4,4,7-Pentamethyl-6-acetyl-chroman (Compound 47)

To an ice-bath cooled solution of 1.96 g (9.6 mmol) of 2,2,4,4,7-pentamethyl-chroman (Compound 46) in 30 ml of nitromethane was added under argon 1.059 g (13.5 mmol) of acetyl chloride followed by 1.9 g (14.3 mmol) of aluminum chloride. The reaction mixture was stirred at room temperature for 14 h and then cooled in an ice-bath and treated with 25 ml of conc. HCl. The mixture was warmed to room temperature and diluted with ether and water. The organic layer was separated and the aqueous layer extracted with ether. The organic extracts were combined and washed successively with water, saturated NaHCO3 solution, water again, and saturated NaCl solution, and then dried (MgSO$_4$). The solvent was removed in vacuo and the residue was purified by flash chromatography (silica; 5% ethyl acetate in hexanes) to give the title compound as a pale yellow oil. PMR (CDCl$_3$): & 1.36 (6 H, s), 1.37 (6 H, s), 1.86 (2 H, s), 2.49 (3 H, s), 2.56 (3 H, s), 6.65 (1 H, s), 7.74 (1 H, s).

2,2,4,4,7-Pentamethyl-6-ethynyl-chroman (Compound 48)

To a solution of 455 mg (4.5 mmol) of disopropylamine in 5 ml of dry THF at −78 degrees C. was added under argon 3 ml of 1.5M n-BuLi in hexane. The mixture was stirred at −78 degrees C. for a further 45 min and then treated with a solution of 1.07 g (4.3 mmol) of 2,2,4,4,7-pentamethyl-6-acetyl-chroman (Compound 47) in 4 ml of dry THF. The reaction mixture was stirred at −78 degrees C. for 1 h and then treated with 776 mg (4.5 mmol) of diethyl chlorophosphate. The mixture was allowed to warm to room temperature and then transferred by a double-ended needle into a solution of lithium diisopropyl amide in 10 ml dry THF at −78 degrees C. which was prepared as described above using 910 mg (9.0 mmol) of diisopropylamine and 6 ml of 1.5M (9.0 mmol) n-BuLi in hexane. The mixture was stirred at room temperature for 15 h and then poured into 10 ml of iced water. The mixture was acidified to pH=2 with 10% HCl solution. The organic layer was separated and the aqueous layer extracted with pentane. The organic extracts were combined and washed successively with water, saturated NaHCO3 and saturated NaCl solutions and then dried (MgSO$_4$). The solvent was removed in vacuo and the residue purified by Kugelrohr distillation (82 degrees C., 0.3 mm) to give the title compound as a pale yellow oil. PMR (CDCl$_3$): & 1.32 (6 H, s), 1.34 (6 H, s), 1.81 (2 H, s), 2.36 (3 H, s), 3.18 (1 H, s), 6.64 (1 H, s), 7.40 1H (s). MS exact mass, m/e 228.1520 (calcd. for C$_{16}$H$_{20}$O, 228.1514).

Ethyl 4-[(2,2,4,4,7-pentamethylchroman-6-yl)-ethynyl] benzoate (Compound 7)

Nitrogen was bubbled for 15 min through a solution of 200 mg. (0.877 mmol) of 2,2,4,4,7-pentamethyl-6-ethynylchroman (Compound 48) and 245.3 mg (0.888 mmol) of ethyl 4-iodobenzoate (Compound 29) in 2 ml of triethylamine. The mixture was then placed under an argon atmosphere and treated with a finely ground mixture of 50 mg (0.2625 mmol) of cuprous iodide and 100 mg (0.1425 mmol) of bis(triphenylphosphine) palladium (II) chloride. The reaction vessel was then fitted with a reflux condenser and the mixture was heated at 55 degrees C. under argon for 72 hours. The triethylamine was then removed under vacuum and the residue purified by flash chromatography (silica, 5% ethyl acetate in hexane) to give the title compound as a yellow oil. PMR (CDCl$_3$) : & 1.32 (12 H, s), 1.37 (3 H, t, J~7.0 Hz), 1.80 (2 H, s) 2.40 (3 H, s), 4.36 (2 H, q, J~7.0 Hz), 6.66 (1 H, s; 7.42 (1 H, s), 7.54 (2 H, d, J~8.6 Hz), 7.99 (2 H, d; J~8.6 Hz). MS exact mass, m/e 376.2 038 (calcd. for C$_{25}$H$_{28}$O$_3$, 376.2038).

2,4,4-Trimethyl-6-Bromo-2-Hydroxy-thiochroman. (Compound 49)

To a solution of 68 g (182.5 mmol) of cerium chloride (dried on a high vacuum line at 135 degrees C. for four days) and 160 ml THF and 62 ml of 3M (186 mmol) methyl magnesium bromide in ether was added to a solution of 5 g (18.45 mmol) of 4-4 dimethyl-6-bromo-2-oxo-thiochroman and 20 ml of dry THF at −14 degrees C. The mixture was stirred for 0.5 hours and then poured onto 300 ml of ice/water mixture containing 10 ml of concentrated sulfuric acid. The layers were separated and the aqueous layer was extracted with 100 ml of ether. The organic layers were combined and washed with 2×250 ml of water, 1×100 ml of saturated sodium chloride solution and then dried (MgSO$_4$). The solvent was removed in vacuo and the residue purified by flash chromatography (silica: 10% EtOAc/Hexanes) to give the title compound as a yellow oil. PMR (CDCl$_3$): & 1.35(3 H, s) 1.47(3 H, s), 1.71(3H. s), 2.09-2.18 (AB doublet), 2.42 (1 H, s), 7.17-7.24 (2 H, m), 7.27 (1 H, d, J=8.1 Hz).

2,4,4, Trimethyl-6-Bromo-(4H)-1-benzothiopyran (Compound 50)

A mixture of 2.03 g (7.1 mmol) of 2,4,4-trimethyl-6-bromo-2-hydroxy thiochroman (Compound 49) and 20 ml of 20% aqueous sulfuric acid was heated at reflux for 4 hours. The mixture was extracted with ether. The combined organic extracts were washed with 2×25 ml H$_2$O and 1×25 ml of saturated NaCl solution and then dried (MgSO$_4$). The solvent was removed in vacuo and the residue purified by flash chromatography (silica; hexanes) to give the title compound as a colorless oil. PMR (CDCl$_3$): & 1.34 (6 H, s), 2.00(3 H, d, J=1.4 Hz), 5.45(1 H, d, J=1.4 Hz), 7.19-7.38 (3 H, m).

2,4,4-trimethyl-6-bromo-thiochroman (Compound 53)

A solution of 500 mg (1.9 mmol) of 2,4,4-trimethyl-6-bromo-(4H)-1-benzothiopyran (Compound 50) in 5 ml of ethyl acetate was treated with 500 mg of 10% palladium sulfide on carbon and then shaken under an atmosphere (30 psi) of hydrogen in a Parr apparatus for 24 hours. The mixture was filtered through celite and the solvent was removed in-vacuo. The residue was purified by flash chromatography (silica; hexanes) to give the title compound as a colorless oil. PMR (CDCl$_3$): & 1.21 (3 H, s), 1.33 (3 H, d, J=6.6 Hz), 1.36 (3 H, s), 1.64-1.89 (2 H, M), 3.37-3.50 (1 H, m), 7.10 (1 H, dd, J=8.4 Hz, 2.1 Hz), 7.19 (1 H, d, 8.4 Hz), 7.20 (1 H, d, 2.1 Hz)

2,4,4-trimethyl-6-trimethylsilyl-ethynyl-thiochroman (Compound 54)

A solution of 201 mg (74 mmol) of 2,4,4-trimethyl-6-bromo-thiochroman (Compound 53) in 1 ml of distilled triethylamine was placed in a heavy walled tube and degassed. The mixture was then treated under argon with 0.53 ml (3.72 mmol) of trimethylsilylacetylene and a powdered mixture of 52 mg (0.074 mmol) of bis-triphenylhosphine palladium (II) chloride and 28 mg (0.15 mmol) of cuprous idodide. The reaction mixture was placed under argon and the tube was sealed. The mixture was heated at 55 degrees C. for 72 hours. The mixture was cooled to room temperature and filtered through celite and the residue washed with CH$_2$Cl$_2$. The filtrate was concentrated in-vacuo and the residue was purified by flash chromatography (silica; hexanes) to give the title compound as a yellow oil. PMR (CDCl$_3$): & 0.24 (9 H, s), 1.22 (3 H, s), 1.33 (3 H, d, J=6.6 Hz), 1.37 (3 H, s), 1.71 (1 H, t, J~13.0 Hz) 1.86 (1 H, dd, J=13.0 Hz, 3.0 Hz) 3.38-3.50 (1 H, m), 7.07 (1 H, dd, J=8.1 Hz, 1.8 Hz), 7.18 (1 H, d, J=1.8 Hz), 7.26 (1 H, d, J=8.1 Hz)

2,4,4-trimethyl-6-ethynyl-thiochroman (compound 55)

To a solution of 186 mg (0.647 mmol) of 2,4,4-trimethyl-6-trimethylsilyl ethynyl thiochroman (Compound 54) was added 11 ml of ethanolic KOH solution. The reaction mixture was stirred at room temperature for 16 hours. The ethanol was then removed in-vacuo and the residue was extracted with ether. The ether extracts were combined and washed with water and saturated sodium chloride solution and then dried (MgSO$_4$). The solvent was removed in-vacuo and the residue purified by Kugelrohr distillation to give the title compound as a colorless oil. PMR (CDCl$_3$): & 1.21 (3 H, s), 1.32 (3 H, d, J=6 Hz), 1.40 (3 H, s,) 1.70 (1 H, t, J~13.0 Hz), 1.88 (1 H, dd, J~13.0 Hz, 3.0 Hz), 3.0 (1 H, s, 3.39-3.51 (1 H, m), 7.13 (1 H, dd, J=9.1 Hz, 2.1 Hz), 7.21 (1 H, d, J~2.1 Hz) 7.28 (1 H, d, J~9.0 Hz).

Ethyl-4[(2,4,4-trimethyl-6-thiochromanyl)-ethynyl] benzoate (Compound 56)

A solution of 55 mg (0.26 mmol) of 2,4,4-trimethyl-6-ethynyl-thiochroman (Compound 55) and 70.5 mg (0.26 mmol) of ethyl 4-iodo benzoate (29) in 1.5 ml of distilled triethylamine was placed in a heavy walled tube. Argon was bubbled through the mixture for 20 minutes under slightly reduced pressure. To the mixture was added 18 mg (0.051 mmol) of bis triphenylphosphine palladium (II) chloride and 9.7 mg (0.051 mmol) of cuprous iodide. The tube was then sealed and the mixture was stirred at 55 degrees C. for 72 hours. The mixture was then cooled to room temperature. The reaction mixture was diluted wth CH$_2$Cl$_2$ and treated with a small amount of silica. The solvent was then removed in-vacuo and the residue was subjected to flash chromatography (silica; 1.5% EtOAc/Hexanes) to give the title compound as a white crystalline solid. PMR(CdCl$_3$): 1.25 (3 H, s), 1.35 (3 H, d, J=6.6 Hz), 1.37-1.44 (6 H, m); 1.75 (1H; t, J=13 Hz), 1.88 (1 H, dd, J=13 Hz, 3.5 Hz), 3.40-3.50 (1 H, m), 4.38 (2 H, q, J=7 Hz), 7.17 (1 H, dd, J=8.1 Hz, 1.8 Hz), 7.26 (1 H, d, J=1.5 Hz), 7.33 (1 H, J=8.1 Hz), 7.55 (2 H, d, J=8.4 Hz, 8.01 (2 H, d, J=8.4 Hz).

4-(2,4,4-trimethyl-6-thiochromanyl)-ethynyl benzoic acid (Compound 57)

A mixture of 37 mg (0.102 mmol) of ethyl 4(2,4,4-trimethyl-6-thiochromanyl)-ethynyl]benzoate (Compound 56) and 11 ml of ethanolic potassium hydroxide solution was stirred at room temperature for 16 hours. The solvent was removed in vacuo and the residue was taken up with water and then acidified with 1N HCl. The mixture was extracted with three portions of ether. The organic extracts were combined and then washed with water and saturated NaCl solution and dried (MgSO₄). The solvent was removed in-vacuo to give the title compound as an orange solid. PMR (CDCl₃): 1.17 (3 H, s), 1.26 (3H; d, J=6.3 Hz), 1.34 (3 H, s), 1.58 (1 H, t, J=13.1 Hz), 1.92 (1 H, dd, J=13.1 Hz, 2.4 Hz), 3.33-3.48 (1 H, m), 7.20 (1 H, d, J=8.1 Hz), 7.21 (1 H, s), 7.45 (1 H, d, J=8.1 Hz), 7.62 (2 H, d, 8.4 Hz), 7.95 (2 H, d, J=8.4 Hz).

Following the procedures set forth above, with such modification and/or application of standard synthetic organic procedure which will be readily apparent to a synthetic organic chemist of ordinary skill, in light of the present disclosure, the following further examples of compounds can be prepared:

2,2,4,4-tetramethyl-6-acetyl-7-ethylchroman;
2,2,4,4-tetramethyl-6-acetyl-7-propylchroman;
2,2,4,4-tetramethyl-6-acetyl-7-butylchroman;
2,2,4,4-tetramethyl-6-acetyl-7-pentylchroman;
2,2,4,4-tetramethyl-6-acetyl-7-hexylchroman;
2,2-diethyl-4,4-dimethyl-6-acetyl-chroman;
2,2-diethyl,-4,4,7-trimethyl-6-acetyl-chroman;
ethyl 4-[(2,2,4,4-tetramethyl-7-ethylchroman-6-yl)ethynyl]benzoate;
ethyl 4-[(2,2,4,4-tetramethyl-7-propylchroman-6-yl)ethynyl]benzoate;
ethyl 4-[(2,2,4,4-tetramethyl-7-hexylchroman-6-yl)ethynyl]benzoate;
ethyl [2-(4-(2,2,4,4-tetramethylchroman-6-yl)ethynyl)phenyl]acetate;
ethyl [2-(4-(2,2,4,4,7-pentamethylchroman-6-yl)ethynyl)phenyl]acetate;
ethyl [2-(4-(2,2,4,4-tetramethyl-7-ethylchroman-6-yl)ethynyl)phenyl]acetate;
ethyl [2-(4-(2,2,4,4-tetramethyl-7-hexylchroman-6-yl)ethynyl)phenyl]acetate;
ethyl 3-[4-((2,2,4,4-tetramethylchroman-2-yl)ethyl)phenyl] propionate;
ethyl 3-[4-((2,2,4,4,7-pentamethylchroman-6-yl)ethynyl)phenyl]propionate;
ethyl 3-[4-(2,2,4,4-tetramethyl-7-ethylchroman-6-yl)ethynyl)phenyl]propionate;
ethyl 3-[4-(2,2,4,4-tetramethyl-7-hexylchroman-6-yl)ethynyl)phenylpropionate;
ethyl 5-[4-((2,2,4,4-tetramethylchroman-6-yl)ethynyl)phenyl]pentanoate;
ethyl 5-[4-((2,2,4,4,7-pentamethylchroman-6-yl)ethynyl)phenyl]pentanoate;
ethyl 5-[4-((2,2,4,4-tetramethyl-7-ethylchroman-6-yl)ethynyl)phenyl]pentanoate;
ethyl 5-[4-((2,2,4,4-tetramethylchroman-6-yl-ethynyl)phenyl]pentanoate;
ethyl 4-[2,2-diethyl-4,4-dimethylchroman-6-yl)ethynyl]benzoate; and
ethyl 4-[2,2-diethyl-4,4,7-trimethylchroman-6-yl)ethynyl]benzoate.

The positional isomers of the above-listed examples can also be prepared in accordance with the foregoing procedures or by such modifications thereof which will be readily apparent to the practicing chemist in light of the foregoing disclosure.

Examples of Formulation for Topical Administration

Preferably the compounds of the invention may be administered topically using various formulations. Such formulations may be as follows:

| Ingredient | Weight/Percent |
|---|---|
| Solution | |
| Retinoid (active ingredient) | 0.1 |
| BHT | 0.1 |
| Alcohol USP | 58.0 |
| Polyesthylene Glycol 400 NF | 41.8 |
| Gel | |
| Retinoid (active ingredient) | 0.1 |
| BHT | 0.1 |
| Alcohol USP | 97.8 |
| Hydroxypropyl Cellulose | 2.0 |

What is claimed is:
1. A process for synthesizing a compound of the formula (I)

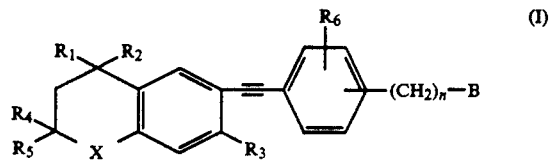

where X is S or O;
$R_1$, $R_2$ and $R_3$ are independently hydrogen or lower alkyl;
$R_4$ and $R_5$ are lower alkyl, with the proviso that $R_4$ and $R_5$ are not the same;
$R_6$ is hydrogen, lower alkyl, lower alkenyl or lower cycloalkyl having 1 to 6 carbons or halogen;
n is an integer from 0 to 5;
B is hydrogen, COOH or a pharmaceutically acceptable salt, ester or amide thereof, —CH₂OH or an ether or ester derivative thereof, or CHO or an acetal derivative thereof, or —COR" or a ketal derivative thereof where R" is an alkyl, cycloalkyl or alkenyl group containing 1 to 5 carbons, the process comprising the steps of:
reacting a compound of formula (II)

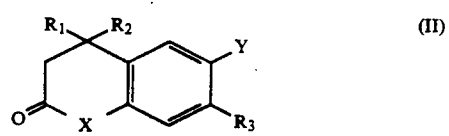

where $R_1$, $R_2$ and $R_3$ are defined as above, and Y is halogen when X is S and Y is hydrogen when X is O, with a Gringnard reagent having the formula $R_4$—Mg—X' where X' is halogen, to obtain a compound of formula (III)

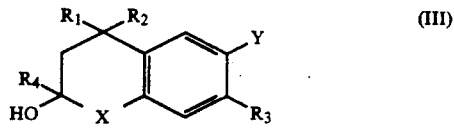

where $R_1$, $R_2$, $R_3$, $R_4$, X and Y are defined as above;
reacting the compound of formula (III) with a Grignard reagent having the formula $R_5$—Mg—X' where $R_5$ and X' are defined as above, to obtain a compound of formula (IV)

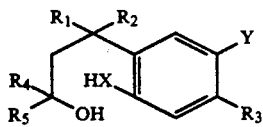

(IV)

where $R_1$, $R_2$, $R_3$, $R_4$, $R_5$, X and Y are defined as above;

converting the compound of formula (IV) to a compound of formula (V)

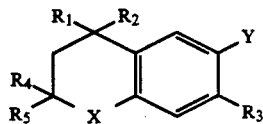

(V)

where $R_1$, $R_2$, $R_3$, $R_4$, $R_5$, X and Y are defined as above;

converting the compound of formula (V) into the compound of formula (I), said steps of converting (V) into (I) when X is S including steps of reacting the compound of formula (V) with a trialkylsilylacetylene and thereafter removing the trialkylsilyl group from the product of that reaction under basic conditions to obtain the compound of formula (VI), when X is O said step of converting including steps of reacting the compound of formula (V) with an acetylating agent under Friedel Crafts conditions, and thereafter reacting the product of that reaction with strong base to obtain the compound of formula (VI), said step of converting further including a step of reacting a compound of formula (VI)

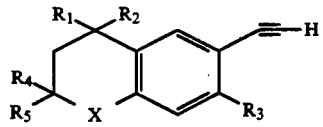

(VI)

where $R_1$, $R_2$, $R_3$, $R_4$, $R_5$ and X are defined as above, with a compound of formula (VII)

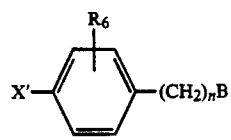

(VII)

where X' is halogen, and $R_6$ and n are defined as above.

2. The process of claim 1 where X is S.
3. The process of claim 1 where X is O.

* * * * *

UNITED STATES PATENT AND TRADEMARK OFFICE
CERTIFICATE OF CORRECTION

PATENT NO. : 5,278,318

DATED : January 11, 1994

INVENTOR(S) : Roshantha A. S. Chandraratna

It is certified that error appears in the above-identified patent and that said Letters Patent is hereby corrected as shown below:

Column 4, line 30, after "$R_4$" insert -- = --;

Column 4, in Formula 6, delete "$R_1$" and "$R_2$";

Column 8, line 46, "reaction" should be --Reaction--;

Column 14, line 56, "scheme" should be --Scheme--;

Column 16, Reaction Schemes 5 and 6, all "S"s in compounds 22,23,51 and 52 should be --O--;

Column 16, line 24, "REACTION SCHEME 4" should be --REACTION SCHEME 6--;

Column 17, line 1, after "6" "." should be --,--;

Column 17, line 44, "3.3" should be --3,3---;

Column 18, line 18, "30M" should be --3.0 M--;

Column 24, line 54, "7.40 1H (s)." should be --7.40 (1H, s).--;

Column 25, line 7, "6.66(1H,s;" should be --6.66(1H, s)--;

Column 25, line 58, "(2H, M)" should be --(2H, m)--;

UNITED STATES PATENT AND TRADEMARK OFFICE
CERTIFICATE OF CORRECTION

PATENT NO. : 5,278,318
DATED : January 11, 1994
INVENTOR(S) : Roshantha A.S. Chandraratna It is certified that error appears in the above-identified patent and that said Letters Patent is hereby corrected as shown below:

Column 26, line 31, "H, s, 3.39" should be --H, s), 3.39--;

Column 27, line 3, ";" should be --,--.

Signed and Sealed this

Ninth Day of August, 1994

Attest:

BRUCE LEHMAN

*Attesting Officer*    Commissioner of Patents and Trademarks

UNITED STATES PATENT AND TRADEMARK OFFICE
CERTIFICATE OF CORRECTION

PATENT NO. : 5,278,318

DATED : January 11, 1994

INVENTOR(S) : Roshantha A.S. Chandraratna

It is certified that error appears in the above-identified patent and that said Letters Patent is hereby corrected as shown below:

Column 21, line 4, before ":" insert --)--;

Column 21, line 56, after "11.92" DELETE ")";

Column 22, line 39, after "6-yl" insert --)--;

Column 23, line 47, "NcCL" should be --NaCL--;

Column 26, line 56, after "J=8.4 Hz" insert --)--.

Signed and Sealed this

Thirteenth Day of September, 1994

Attest:

BRUCE LEHMAN

Attesting Officer　　　Commissioner of Patents and Trademarks